(12) United States Patent
Yang et al.

(10) Patent No.: US 12,115,238 B2
(45) Date of Patent: Oct. 15, 2024

(54) COSMETIC COMPOSITION IN MULTIPLE EMULSION FORMULATION

(71) Applicant: AMOREPACIFIC CORPORATION, Seoul (KR)

(72) Inventors: Heejung Yang, Yongin-si (KR); Byungfhy Suh, Yongin-si (KR); Soonae An, Yongin-si (KR); Joonyoung Hwang, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 753 days.

(21) Appl. No.: 17/291,509

(22) PCT Filed: Nov. 8, 2019

(86) PCT No.: PCT/KR2019/015167
§ 371 (c)(1),
(2) Date: May 5, 2021

(87) PCT Pub. No.: WO2020/096414
PCT Pub. Date: May 14, 2020

(65) Prior Publication Data
US 2021/0393490 A1    Dec. 23, 2021

(30) Foreign Application Priority Data

Nov. 8, 2018  (KR) .................... 10-2018-0136458
Jul. 31, 2019  (KR) .................... 10-2019-0093056
Nov. 6, 2019  (KR) .................... 10-2019-0141267

(51) Int. Cl.
*A61K 8/06*    (2006.01)
*A61K 8/31*    (2006.01)
(Continued)

(52) U.S. Cl.
CPC ............. *A61K 8/066* (2013.01); *A61K 8/31* (2013.01); *A61K 8/345* (2013.01); *A61K 8/37* (2013.01);
(Continued)

(58) Field of Classification Search
None
See application file for complete search history.

(56) References Cited

U.S. PATENT DOCUMENTS 6,391,288 B1    5/2002    Miyazawa et al.

FOREIGN PATENT DOCUMENTS

EP    0782846 B1    7/1997
EP    1 369 101 A1    12/2003
(Continued)

OTHER PUBLICATIONS

KR100722677B1—Google English translation (Year: 2007).*
(Continued)

*Primary Examiner* — Kyung S Chang
(74) *Attorney, Agent, or Firm* — Sughrue Mion, PLLC

(57) ABSTRACT

A cosmetic composition containing a multiple emulsion formulation is provided. The multiple emulsion formulation contains droplets including an inner phase and an outer phase and an outermost phase, and an outermost phase. The inner phase may be an oil phase and the outer phase may be an aqueous phase, and the outermost phase includes silicon-based oil. The cosmetic composition may provide excellent formulation stability due to the distribution of the droplets very close to the outermost phase.

25 Claims, 6 Drawing Sheets

(51) Int. Cl.
    *A61K 8/34*     (2006.01)
    *A61K 8/37*     (2006.01)
    *A61K 8/41*     (2006.01)
    *A61K 8/81*     (2006.01)
    *A61K 8/86*     (2006.01)
    *A61K 8/891*     (2006.01)
    *A61Q 19/00*     (2006.01)

(52) U.S. Cl.
    CPC .............. *A61K 8/41* (2013.01); *A61K 8/8152* (2013.01); *A61K 8/86* (2013.01); *A61K 8/891* (2013.01); *A61Q 19/00* (2013.01); *A61K 2800/20* (2013.01); *A61K 2800/412* (2013.01); *A61K 2800/48* (2013.01); *A61K 2800/54* (2013.01); *A61K 2800/594* (2013.01); *A61K 2800/596* (2013.01); *A61K 2800/805* (2013.01)

(56) References Cited

FOREIGN PATENT DOCUMENTS

| | | |
|---|---|---|
| JP | 2001-354515 A | 12/2001 |
| JP | 2006-273747 A | 10/2006 |
| JP | 3939821 B2 | 7/2007 |
| JP | 4125463 B2 | 7/2008 |
| KR | 10-0541753 B1 | 6/2001 |
| KR | 10-2004-0020092 A | 3/2004 |
| KR | 10-2005-0097587 A | 10/2005 |
| KR | 10-1133067 B1 | 5/2007 |
| KR | 100722677 B1 * | 5/2007 |
| KR | 10-0874877 B1 | 9/2008 |
| KR | 10-1655346 B1 | 6/2011 |
| KR | 10-2012-0027788 A | 3/2012 |
| KR | 10-2013-0087332 A | 8/2013 |
| KR | 10-2016-0116877 A | 10/2016 |
| KR | 10-2018-0003138 A | 1/2018 |
| KR | 10-2018-0121251 A | 11/2018 |
| WO | 2011/065771 A2 | 6/2011 |

OTHER PUBLICATIONS

Extended European Search Report dated Aug. 4, 2022 in European Application No. 19882021.9.
International Searching Authority, International Search Report for PCT/KR2019/015167 dated Feb. 21, 2020 [PCT/ISA/210].
International Searching Authority, Written Opinion for PCT/KR2019/015167 dated Feb. 21, 2020 [PCT/ISA/237].
Communication dated Jun. 26, 2023, issued in Korean Application No. 10-2019-0141267.
Communication dated Jun. 26, 2023, issued in Korean Application No. 10-2018-0136458.
Communication dated Mar. 28, 2024 issued by the European Patent Office in application No. 19882021.9.

* cited by examiner

COSMETIC COMPOSITION IN MULTIPLE EMULSION FORMULATION

CROSS-REFERENCE TO RELATED APPLICATIONS

This application is a National Stage of International Application No. PCT/KR2019/015167 filed Nov. 8, 2019, which claims priority to Korean Patent Application No. 10-2018-0136458 filed on Nov. 8, 2018, Korean Patent Application No. 10-2019-0093056 filed on Jul. 31, 2019, and Korean Patent Application No. 10-2019-0141267 filed on Nov. 6, 2019.

TECHNICAL FIELD

The present specification describes a cosmetic composition having a stable multiple emulsion formulation.

BACKGROUND ART

In cosmetic compositions of multiple emulsion formulations such as O/W/O (Oil-in-Water-in-Oil) or W/O/W (Water-in-Oil-in-Water), generally, a surfactant has been used as an emulsifier in inner and outer phases; however, in this case, there is a drawback that the formulation itself is structurally complicated and thermodynamically unstable. This is because, in the case of conventional emulsion formulations in which a surfactant is used in inner and outer phases, due to the Laplace effect, interfacial tension acts towards a side where the surface area of droplets dispersed in a continuous phase is to be minimized, and thereby the pressure of the droplets in the inner phase is higher than the pressure of the droplets in the outer phase, and the pressure difference gives a force to move the droplets in the inner phase to the outer phase, which makes the multiple emulsion formulation unstable.

CITATION LIST

Patent Literature

[Patent Literature 1]
Korean Patent Laid-Open No. 10-2005-0097587

Non-Patent Literature

[Non-Patent Literature 1]
Ferreira T and Rasband WS. "Image) User Guide—IJ 1.46", imagej.nih.gov/ij/docs/guide/, 2010-2012

SUMMARY OF INVENTION

Technical Problem

In one aspect, the object of the present invention is to provide a cosmetic composition of a multiple emulsion formulation with excellent formulation stability.

Solution to Problem

In order to achieve the object, one embodiment of the present invention provides a cosmetic composition of a multiple emulsion formulation, comprising droplets comprising an inner phase and an outer phase; and an outermost phase, wherein said composition satisfies one or more of following (i) to (iii):

(i) a distance between two adjacent droplets distributed in the formulation is 5 μm or less, and the distance is calculated for droplets having an average particle size of 2 μm to 50 μm, the distance between the droplets being calculated by Equation 1:

$$\text{Distance between the droplets} = (A) - (r+R) \quad \text{[Equation 1]}$$

where in Equation 1, A represents a distance between the centers of the two adjacent droplets of the composition, and r and R represent the respective radius of the two adjacent droplets, measured on the same line as A;

(ii) in a microscopy image obtained by taking a photography of the composition, the sum of the areas of the droplets distributed in the formulation with respect to 100% of the total area of the image is 80% or more and less than 100%, the microscopy image being taken at a magnification of 1000; and (iii) the amount of the droplets comprising the inner phase and the outer phase is greater than 80 wt. % to less than 100 wt. % with respect to the total weight of the composition.

Advantageous Effects of Invention

The cosmetic composition according to the present invention has a structure where droplets distributed in the outermost phase of the formulation are very dense to be adjacent. The present invention is capable of stably maintaining the multiple emulsion formulation of the inner phase—the outer phase—the outermost phase, as the adjacent droplets have a force pushing against each other in the outermost phase. Since the present invention has the multiple emulsion formulation as above, the present invention can comprise skin-useful ingredients, which have low solubility or low stability, stably in the inner phase. In addition, when using the present invention, the droplets in the formulation burst, which can give fresh hydrating feeling and moisturizing feeling, as if waterdrops burst on the skin.

DESCRIPTION OF EMBODIMENTS

The present invention relates to a cosmetic composition of a multiple emulsion formulation. Hereinafter, the examples of the present invention will be explained in detail with reference to the drawings attached herewith.

One embodiment of the present invention provides a cosmetic composition of a multiple emulsion formulation, comprising: droplets comprising an inner phase and an outer phase; and an outermost phase.

Figure 1:
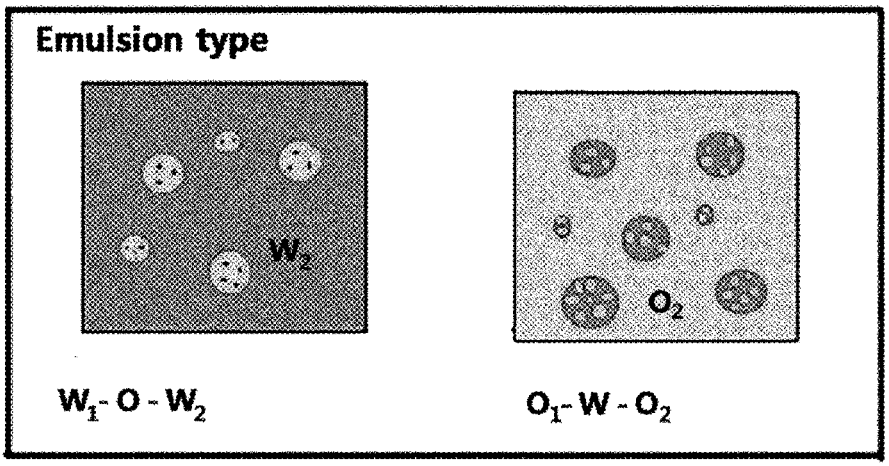
FIG. 1 is a schematic diagram of W/O/W (Water-in-Oil-in-Water) and O/W/O (Oil-in-Water-in-Oil) formulations as conventional cosmetic compositions of multiple emulsion formulations.
Figure 2:
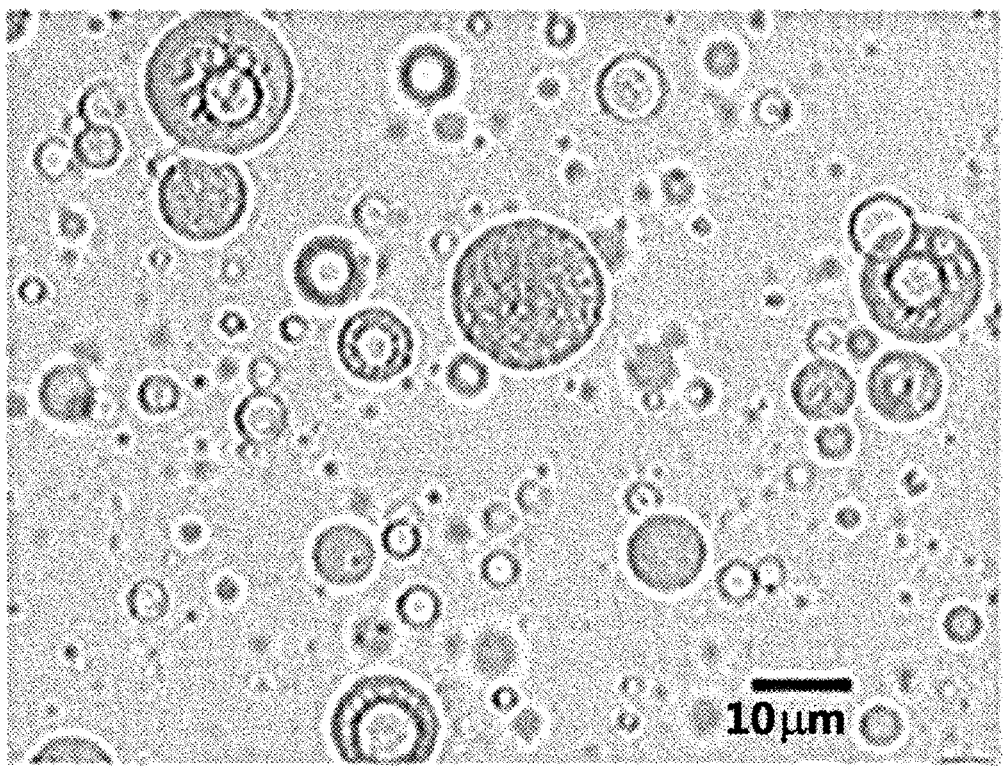
FIG. 2 is a microscopy image of an O/W/O (Oil-in-Water-in-Oil) formulation as a conventional cosmetic composition of a multiple emulsion formulation (scale bar 10 μm).
Figure 3:
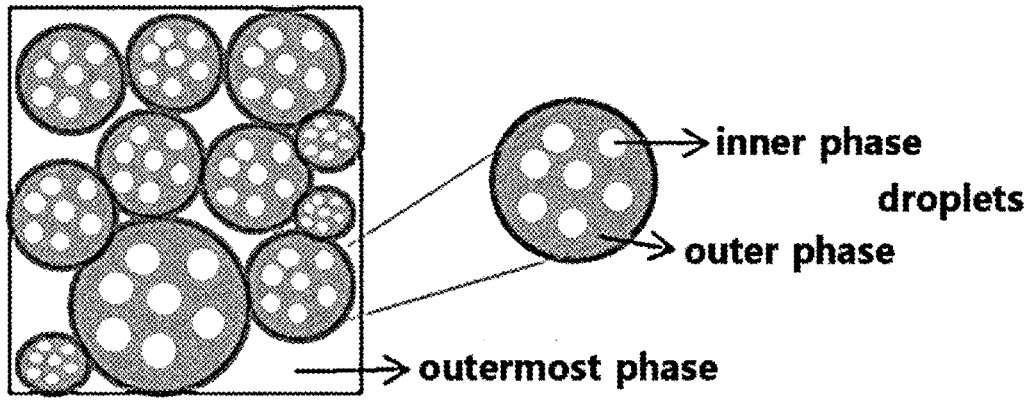
FIG. 3 is a schematic diagram of a cosmetic composition of a multiple emulsion formulation according to one embodiment of the present invention.
Figure 4:
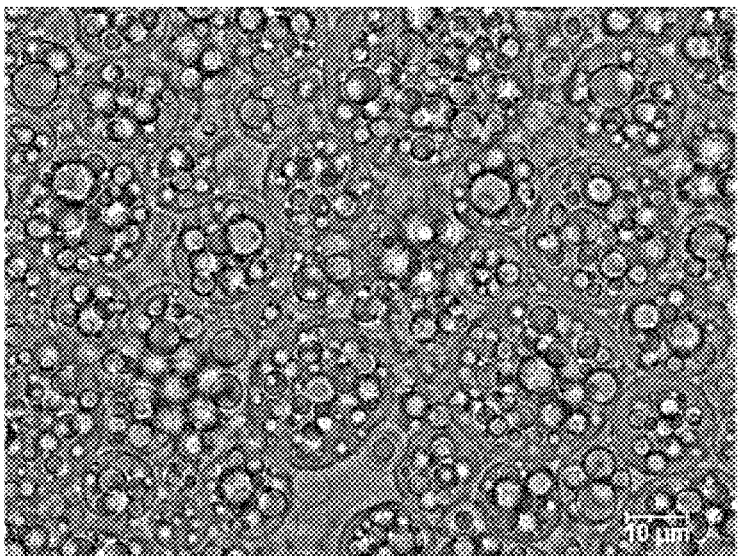
FIG. 4 is a microscopy image of the cosmetic composition of a multiple emulsion formulation according to one embodiment of the present invention (scale bar 10 μm).

FIGS. 1 and 2 attached illustrate the exemplary forms of the conventional cosmetic compositions of multiple emulsion formulations, and FIGS. 3 and 4 illustrate the exemplary forms of the present invention. Referring to FIGS. 1 and 2, the conventional multiple emulsion formulations such as W/O/W (Water-in-Oil-in-Water) and O/W/O (Oil-in-Water-in-Oil) illustrated in FIG. 1 have a structure where droplets comprising an inner phase and an outer phase are scattered in an aqueous or oil outermost phase. By contrast, as illustrated in FIGS. 3 and 4, the composition according to the embodiments of the present invention has a structure where droplets comprising an inner phase and an outer phase in the formulation are very adjacent or close to each other, so the force pushing the droplets against each other maintains the formulation stably, and thereby, no phase separation of the composition occurs even for a long-term storage.

In one embodiment of the present invention, the composition may satisfy that in a microscopy image obtained by taking a photograph of the composition, the sum of the areas of the droplets distributed in the formulation with respect to 100% of the total area of the image is 80% or more and less than 100%. Herein, the microscopy image may be taken at a magnification of 1000. In one embodiment, the microscopy image is obtained by preparing the composition, storing it at 25° C., and taking a photograph of the composition using a microscope (manufacturer: Nikon, Model Name: Eclipse 80i Microscope).

According to one embodiment, any method of analyzing the sum of the areas of the droplets from the microscopy image can be used without limitation as long as the sum of the areas of the droplets can be calculated. According to one embodiment, the method of calculating the sum of the areas of the droplets from the microscoye image may comprise calculating using Image-Pro® 10 Image Analysis Software program (manufacturer: MEDIA CyberNetics). According to one embodiment, the method of calculating the sum of the areas of the droplets from the microscopy image may comprise calculating using an image processing and an analysis program, Image J, which is provided by the US National Institutes of Health (NIH). The Image J can be downloaded from the website https://imagej.nih.gov/ij/. The method of using Image J is explained in Ferreira T and Rasband WS. "Image) User Guide—IJ 1.46", imagej.nih-.gov/ij/docs/guide/, 2010-2012, and the above document is incorporated by reference in the present specification as a whole.

The microscopy image may have a size of 700 μm×500 μm, and have a rectangular shape. In one embodiment, the total area of the droplets distributed in the formulations with respect to 100% of the total area of the composition may be 80% or more, 81% or more, 82% or more, 83% or more, 84% or more, 85% or more, 86% or more, 87% or more, 88% or more, 89% or more, 90% or more, 91%, 92% or more, 93% or more, 94% or more, 95% or more, 96% or more, 97% or more, 98% or more, or 99% or more.

The size of the droplets comprised in the composition of the present invention and the density between the droplets can be properly adjusted by a user in order to provide a stable formulation without phase separation.

According to one embodiment, the average particle size of the droplets comprised in the present invention may be 2 μm to 50 μm. In the specification of the present invention, the particle size of the droplets means the largest diameter in the particles, and the average particle size of the droplets means the average particle size of at least 90% of the droplets distributed in the composition. Specifically, the average particle size of the droplets is a value obtained by selecting, from the droplets distributed in the composition, droplets corresponding to at least 90% or more, 91% or more, 92% or more, 93% or more, 94% or more, 95% or more, 96% or more, 97% or more, 98% or more, or 99% or more with respect to the total number of the droplets, and calculating the average of the largest diameter values measured in each of the particle. More specifically, the average particle size may be 2 μm or more, 3 μm or more, 4 μm or more, 5 μm or more, 6 μm or more, 7 μm or more, 8 μm or more, 9 μm or more, 10 μm or more, 11 μm or more, 12 μm or more, 13 μm or more, 14 μm or more, 15 μm or more, 16 μm or more, 17 μm or more, 18 μm or more, 19 μm or more, 20 μm or more, 21 μm or more, 22 μm or more, 23 μm or more, 24 μm or more, 25 μm or more, 26 μm or more, 27 μm or more, 28 μm or more, 29 μm or more, 30 μm or more, 31 μm or more, 32 μm or more, 33 μm or more, 34 μm or more, 35 μm or more, 36 μm or more, 37 μm or more, 38 μm or more, 39 μm or more, 40 μm or more, 41 μm or more, 42 μm or more, 43 μm or more, 44 μm or more, 45 μm or more, 46 μm or more, 47 μm or more, 48 μm or more, 49 μm or more, or 49.9 μm or more. Or, the average particle size may be 50 μm or less, 49 μm or less, 48 μm or less, 47 μm or less, 46 μm or less, 45 μm or less, 44 μm or less, 43 μm or less, 42 μm or less, 41 μm or less, 40 μm or less, 39 μm or less, 38

µm or less, 37 µm or less, 36 µm or less, 35 µm or less, 34 µm or less, 33 µm or less, 32 µm or less, 31 µm or less, 30 µm or less, 29 µm or less, 28 µm or less, 27 µm or less, 26 µm or less, 25 µm or less, 24 µm or less, 23 µm or less, 22 µm or less, 21 µm or less, 20 µm or less, 19 µm or less, 18 µm or less, 17 µm or less, 16 µm or less, 15 µm or less, 14 µm or less, 13 µm or less, 12 µm or less, 11 µm or less, 10 µm or less, 9 µm or less, 8 µm or less, 7 µm or less, 6 µm or less, 5 µm or less, 4 µm or less, 3 µm or less, or 2 µm or less.

According to one embodiment, the distance between two adjacent droplets in the formulation may be 5 µm or less, wherein the distance between the droplets may be calculated by Equation 1.

$$\text{Distance between the droplets} = (A) - (r+R) \quad \text{[Equation 1]}$$

where in Equation 1, A represents a distance between the centers of the two adjacent droplets of the composition, and r and R represent the respective radius of the two adjacent droplets measured on the same line as A. Herein, the radius means the distance from the center of the droplets to the interface.

According to one embodiment, in the present specification, the term "adjacent" means that no other droplet is present between two droplets, and herein, the droplets all mean droplets comprising an inner phase and an outer phase.

According to one embodiment, the distance between two adjacent droplets in the formulation is measured for at least 90% or more of droplets with respect to the total number of the droplets distributed in the composition. Specifically, the distance between the droplets may be obtained by selecting, from the droplets distributed in the specification, droplets corresponding to at least 90% or more, 91% or more, 92% or more, 93% or more, 94% or more, 95% or more, 96% or more, 97% or more, 98% or more, or 99% or more with respect to the total number of the droplets, and measuring the distance between two adjacent droplets among these droplets.

According to one embodiment, the distance may be calculated for the droplets having an average particle size of between 2 µm and 50 µm.

According to one embodiment, the distance between the two adjacent droplets in the formulation may be average 5 µm or less, 4.5 µm or less, 4 µm or less, 3.5 µm or less, 3 µm or less, 2.5 µm or less, 2 µm or less, 1.5 µm or less, 1 µm or less, 0.5 µm or less, or 0.1 µm or less, and may be average 0 µm or more, 0.1 µm or more, 0.5 µm or more, 1.0 µm or more, 1.5 µm or more, 2.0 µm or more, 2.5 µm or more, 3 µm or more, 4 µm or more, or 4.9 µm or more.

According to one embodiment, the content of the droplets comprised in the composition of the present invention is not limited as long as the droplets can have a uniformly dense structure, and may be appropriately adjusted by a user to provide a stable formulation. For example, the droplets may be comprised in an amount of more than 80 wt. %, 81 wt. % or more, 82 wt. % or more, 83 wt. % or more, 84 wt. % or more, 85 wt. % or more, 86 wt. % or more, 87 wt. % or more, 88 wt. % or more, 89 wt. % or more, 90 wt. % or more, 91 wt. % or more, 92 wt. % or more, 93 wt. % or more, 94 wt. % or more, 95 wt. % or more, 96 wt. % or more, 97 wt. % or more, 98 wt. % or more, or 99 wt. % or more, with respect to the total weight of the composition. Or, for example, the oil-in-water droplets may be comprised in an amount of less than 100 wt. %, 99 wt. % or less, 98 wt. % or less, 97 wt. % or less, 96 wt. % or less, 95 wt. % or less, 94 wt. % or less, 93 wt. % or less, 92 wt. % or less, 91 wt. % or less, 90 wt. % or less, 89 wt. % or less, 88 wt. % or less, 87 wt. % or less, 86 wt. % or less, 85 wt. % or less, 84 wt. % or less, 83 wt. % or less, 82 wt. % or less, or 81 wt. % or less, with respect to the total weight of the composition. Or, according to one embodiment, the droplets comprising an inner phase and an outer phase may be comprised in an amount of more than 80 wt. % to less than 100 wt. %, specifically more than 80 wt. % to 95 wt. % or less, more specifically, 85 wt. % to 90 wt. % or 90 wt. % to 95 wt. %, with respect to the total weight of the composition.

According to one embodiment of the present invention, the multiple emulsion formulation may be an O/W/S (Oil-in-Water-in-Silicon Oil) formulation comprising the inner phase which is an oil phase; the outer phase which is an aqueous phase; and the outermost phase comprising silicon-based oil.

According to one embodiment of the present invention, the inner phase of the composition may comprise oils, and the types of oils may be, but not limited to, ester-based oils, hydrocarbon-based oils, oils of natural origin, silicon-based oils, etc., or mixtures thereof. Specifically, the inner phase may comprise one or more oils selected from the group consisting of squalane, caprylic/capric triglyceride, cetyl ethylhexanoate, 2-octyldodecanol, and pentaerythritol tetra-2-ethylhexanoate, etc., or mixtures thereof. According to one embodiment, the inner phase may further comprise, in addition to oils, active ingredients such as whitening agents, wrinkle-improving agents, UV blocking agents, antioxidants, etc., as useful ingredients. According to one embodiment, the outer phase may also comprise moisturizing agents, whitening agents, wrinkle-improving agents, UV blocking agents, antioxidants, etc., or mixtures thereof as aqueous ingredients. For example, the inner phase may further comprise one or more active ingredients selected from the group consisting of thymol trimethoxycinnamate, oil-soluble vitamin, fat-soluble bioactive ingredient, oil-soluble licorice and polyphenol. As specific examples, the thymol trimethoxycinnamate may be Melasolv™ (AMOREPACIFIC CORPORATION), and the oil-soluble vitamin may comprise one or more of retinol and tocopherol. The fat-soluble bioactive ingredient may comprise one or more of linolenic acid and glycolipid.

According to one embodiment of the present invention, the outer phase of the composition may comprise polyol.

Polyol comprised as one embodiment may refer to polyhydric alcohols, for example, fatty alcohols having two or more hydroxyl groups (—OH). Alcohols having two hydroxyl groups are called glycol or diol, alcohols having three hydroxyl groups are called triol (for example, glycerol), and alcohols having four hydroxyl groups are called tetraol (for example, pentaerythritol). According to one embodiment, the polyol may comprise one or more selected from the group consisting of polyethylene glycol, polypropylene glycol, dipropylene glycol, propylene glycol, butylene glycol, glycerin, polyglycerin-3, propanediol, sorbitol, erythritol, xylitol, maltitol, ethylhexanediol, 1,2-hexanediol, PEG/PPG/polybutylene glycol-8/5/3 glycerin, and pentylene glycol. The amount of the polyol comprised in the cosmetic composition of the present invention is not limited and can be properly adjusted by a user. According to one embodiment, the polyol may be comprised in an amount of 1 wt. % or more, 2 wt. % or more, 3 wt. % or more, 4 wt. % or more, 5 wt. % or more, 6 wt. % or more, 7 wt. % or more, 8 wt. % or more, 9 wt. % or more, 10 wt. % or more, 11 wt. % or more, 12 wt. % or more, 13 wt. % or more, 14 wt. % or more, 15 wt. % or more, 16 wt. % or more, 17 wt. % or more, 18 wt. % or more, 19 wt. % or more, 20 wt. % or more, 21 wt. % or more, 22 wt. % or more, 23 wt. % or more, 24 wt. % or more, 25 wt. % or more, 26 wt. % or more, 27 wt. % or more, 28 wt. % or more, 29 wt. % or more, or 30 wt. % or more, with respect to the total weight of the composition. In addition, according to one embodiment, the polyol may be comprised in an amount of 30 wt. % or less, 29 wt. % or less, 28 wt. % or less, 27 wt. % or less, 26 wt. % or less, 25 wt. % or less, 24 wt. % or less, 23 wt. % or less, 22 wt. % or less, 21 wt. % or less, 20 wt. % or less, 19 wt. % or less, 18 wt. % or less, 17 wt. % or less, 16 wt. % or less, 15 wt. % or less, 14 wt. % or less, 13 wt. % or less, 12 wt. % or less, 11 wt. % or less, 10 wt. % or less, 9 wt. % or less, 8 wt. % or less, 7 wt. % or less, 6 wt. % or less, 5 wt. % or less, 4 wt. % or less, 3 wt. % or less, 2 wt. % or less, or 1 wt. % or less, with respect to the total weight of the composition. Or, according to one embodiment, the composition may comprise the polyol in an amount of 1 to 30 wt. %, for example, 15 wt. % to 25 wt., with respect to the total weight of the composition. According to one embodiment, the composition may comprise the polyol in an amount of 5 wt. % to 35 wt. %, for example, 20 wt. % to 30 wt. %, with respect to the total weight of the outer phase.

According to one embodiment, the outer phase may further comprise a thickener and/or a solvent. According to one embodiment, the solvent comprised in the outer phase may comprise one or more of water and ethanol, preferably water, more preferably water and ethanol. According to one embodiment, the outer phase may comprise the ethanol in an amount of 3 to 10 wt. %, for example, 4 to 9 wt. %, for example, 5 to 9 wt. %, for example, 6 to 8 wt. %, with respect to the total weight of the composition, in order to lower the freezing point to −15° C. or below so that the composition of the present invention is not frozen even for cold storage. According to one embodiment, the ethanol may be comprised in an amount of 5 wt. % to 12 wt. % with respect to the total weight of the outer phase. In case where the freezing point is low, the possibility of water in the aqueous phase comprised in the outer phase in the formulation of the composition being frozen, the particles being swollen, thereby separating the formulation is reduced, and thereby the formulation can be maintained more stably.

In addition, according to one embodiment, the outer phase may further comprise other water-soluble moisturizing agents and water-soluble active ingredients, etc. For example, the outer phase may comprise one or more selected from the group consisting of betaine, niacinamide, adenosine, sodium hyaluronate, D-panthenol, tranexamic acid, glycerin, butylene glycol, derivatives such as vitamin C, arbutin, and Fructose-1,6-diphosphate trisodium salt.

According to one embodiment, the thickener comprised in the outer phase may comprise all water-soluble thickeners that can be dissolved in the solvent without any limitation. Specifically, the thickener may comprise one or more of polyacrylate-based polymer and natural thickeners. For example, the polyacrylate-based polymer may comprise one or more selected from the group consisting of carbomer, acrylate/C10-30 alkyl acrylate crosspolymer, ammonium acryloyl dimethyltaurate/VP copolymer, hydroxylethylacrylate/sodium acryloyl dimethyltaurate copolymer, sodium polyacrylate and polyacrylate-13. Since carbomer is not hydrophobic, this cannot hold the oil-phase ingredients in the inner phase when it is comprised alone, and thereby, stability is low. The other polyacrylate-based polymer which has a hydrophobic chain can hold the oil-phase ingredient, but this causes a clotty phenomenon when it is comprised alone. For this reason, the composition according to one embodiment of the present invention may comprise, as the thickener, carbomer and a polyacrylate-based polymer which has a hydrophobic chain together, thereby providing excellent dispersion and stability of the oil-in-water droplet inner and outer phases. According to one embodiment, the ratio of the carbomer and the polyacrylate-based polymer may be 1:0.5 to 1.5, more specifically, about 1:1. According to one embodiment, the natural thickeners may comprise saccharide thickeners. According to one embodiment, the natural thickeners may comprise one or more selected from the group consisting of cellulose gum, hydropropyl methyl cellulose, xanthan gum, and *Ceratonia siliqua* gum, but are not limited thereto. According to one embodiment, the thickener may be comprised in an amount of 0.01 to 1.0 wt. %, more specifically, 0.05 to 0.5 wt. %, with respect to the total weight of the composition. According to one embodiment, the thickener may be comprised in an amount of 0.02 to 1.3 wt. %, for example, 0.06 to 0.7 wt. %, with respect to the total weight of the outer phase.

According to one embodiment, the droplets comprising an inner phase and an outer phase comprised in the composition according to the present invention may be surfactant-free, which does not substantially comprise a surfactant, and specifically may comprise the surfactant in an amount of 1 wt. % or less, 0.1 wt. % or less, or 0.01 wt. % or less, with respect to the total weight of the droplets. As such, the composition according to the present invention may not comprise a surfactant in the droplets comprising the inner phase and the outer phase, but may comprise the thickener instead, thereby maintaining the multiple emulsion formulation comprising the inner phase—the outer phase—the outermost phase stably.

According to one embodiment, the droplets may further comprise a neutralizer. For example, the neutralizer may comprise salts, for example, sodium hydroxide, potassium hydroxide, L-arginine, triethanolamine, tromethamine, etc., or mixtures thereof.

In the multiple emulsion formulation comprising droplets comprising an inner phase and an outer phase, and an outermost phase according to one embodiment of the present invention, the sum of the amounts of the outermost phase and an interface of the outermost phase may be more than 0 wt. % to less than 20 wt. % with respect to the total weight of the composition. Specifically, the sum of the amounts of the outermost phase and an interface of the outermost phase may be comprised in an amount of 0.01 wt. % or more, 0.05 wt. % or more, 0.1 wt. % or more, 0.2 wt. % or more, 0.3 wt. % or more, 0.4 wt. % or more, 0.5 wt. % or more, 0.6 wt. % or more, 0.7 wt. % or more, 0.8 wt. % or more, 0.9 wt. % or more, 1 wt. % or more, 2 wt. % or more, 3 wt. % or more, 4 wt. % or more, 5 wt. % or more, 6 wt. % or more, 7 wt. % or more, 8 wt. % or more, 9 wt. % or more, 10 wt. % or more, 11 wt. % or more, 12 wt. % or more, 13 wt. % or more, 14 wt. % or more, 15 wt. % or more, 16 wt. % or more, 17 wt. % or more, 18 wt. % or more, or 19 wt. % or more, with respect to the total weight of the composition, and may be comprised in an amount of 19.9 wt. % or less, 19 wt. % or less, 18 wt. % or less, 17 wt. % or less, 16 wt. % or less, 15 wt. % or less, 14 wt. % or less, 13 wt. % or less, 12 wt. % or less, 11 wt. % or less, 10 wt. % or less, 9 wt. % or less, 8 wt. % or less, 7 wt. % or less, 6 wt. % or less, 5 wt. % or less, 4 wt. % or less, 3 wt. % or less, 2 wt. % or less, 1 wt. % or less, 0.5 wt. % or less, or 0.1 wt. % or less, with respect to the total weight of the composition.

According to one embodiment, the silicon-based oil comprised in the outermost phase may comprise one or more selected from the group consisting of dimethicone, trimethicone, methyltrimethicone, phenyltrimethicone, amodimethicone, cyclomethicone, dimethiconol, vinyldimethicone, propoxytetramethylpiperidinyl dimethicone, cyclotetrasiloxane, cyclopentasiloxane, cyclohexasiloxane, methyletherdimethylsilane, and a copolymer thereof.

According to one embodiment, an interface of the outermost phase and the outer phase may comprise a silicon-based surfactant. Specifically, the silicon-based surfactant has an HLB (hydrophile-lipophile balance) of 7 or less. The HLB is obtained by the calculation method of Griffin. More specifically, the silicon-based surfactant may be a silicon-based surfactant in which polyethylene glycol (PEG) is combined, and comprise one or more of cyclopentasiloxane/dimethicone/dimethicone/PEG-10/15 crosspolymer and cetyl PEG/PPG-10/1 dimethicone/pentaerythrityl tetra-di-t-butyl hydroxyhydrocinnamate. Or, it may be a silicon-based surfactant in which polyglycerin is combined, and comprise one or more of lauryl dimethicone/polyglycerin-3 crosspolymer, lauryl polyglyceryl-3 polydimethylsiloxyethyl dimethicone, polyglyceryl-3 polydimethylsiloxyethyl dimethicone, polyglyceryl-3 disiloxane dimethicone and dimethicone/polyglycerin-3 crosspolymer. According to one embodiment, as the present invention may comprise the silicon-based surfactant in the outermost phase, the distance between the two adjacent droplets in the formulation of the present invention may maintain an average of 5 μm or less, and the multiple emulsion formulation of the inner phase—the outer phase—the outermost phase may be stably maintained. According to one embodiment, the present invention can provide the multiple emulsion formulation of the inner phase—the outer phase—the outermost phase even without comprising a thickener in the outermost phase, wherein the distance between the two adjacent droplets in the formulation is an average of 5 μm or less, and can further comprise a thickener in the outermost phase by the user's selection depending on the desired formulation. According to one embodiment, the formulation which does not comprise a thickener in the outermost phase can give fresh feeling in use.

A method for preparing the multiple emulsion cosmetic composition of the present invention described above as one embodiment may comprise: a step of preparing droplets by introducing an inner phase into an outer phase; and a step of stabilizing by introducing the droplets into the outermost phase. More specifically, the preparation method may comprise: a first emulsifying step of preparing oil-in-water droplets by introducing an outer phase ingredient comprising polyol and a thickener into a solvent as the outer phase and dispersing it, and then introducing an oil ingredient comprising oil, etc. into the outer phase; and a second emulsifying step of stabilizing by introducing the droplets into the outermost phase comprising silicon-based oil and a silicon-based surfactant.

According to one embodiment, the first emulsifying step may be carried out by polymer emulsification in which a surfactant is not used. According to one embodiment, the first emulsifying step may be performed by stirring, for example, at 2,000 to 4,000 rpm for 1 to 5 minutes. According to one embodiment, the first emulsifying step may comprise, for example, introducing the oil to the outer phase and then stirring at for example, 2,000 to 5,000 rpm, for example, 3,000 to 4,000 rpm, for, for example, 1 to 5 minutes.

According to one embodiment, the method may comprise, at the first emulsifying step, introducing the oil ingredient and carrying out the polymer emulsification, and then introducing a neutralizer. According to one embodiment, after introducing the neutralizer, stable droplets can be prepared by stirring it.

In addition, the second emulsifying step may be carried out by the HIPE (high internal phase emulsion) emulsification method. As the present invention uses the HIPE emulsification method, the freezing point of the inner phase can be lowered, thereby improving stability in the multiple emulsion formulation.

According to one embodiment, the cosmetic composition according to the present invention may be a cosmetic composition for skin moisturizing.

An embodiment of the present invention may relate to the use of the above-described cosmetic composition as a cosmetic, and specifically, the cosmetic may be for skin moisturizing.

In addition, the cosmetic composition may preferably comprise, in addition to said ingredients, other ingredients which can give synergistic effects to the main effect within the range which does not impair the main effect. The ingredients other than the effective ingredients of the present invention can be properly selected and blended by a user without any difficulty depending on the formulation or use purpose of the cosmetic composition. In addition, according to one embodiment, the cosmetic composition of the present invention may comprise other ingredients that are blended in typical cosmetic compositions as needed. For example, the other ingredients may be moisturizing agents, emollient, organic and inorganic pigments, organic powder, ultraviolet absorbent, antimicrobial agent, sterilizer, antioxidant, herb extract, pH adjuster, alcohols, colorant, perfume, blood circulating promoter, cooling agent, antiperspirant, purified water, etc. The other ingredients that can be comprised in the cosmetic composition of the present invention are not limited thereto, and the amount of the ingredients blended may be possible within the range that does not impair the object and effects of the present invention.

According to one embodiment, the formulations of the cosmetic composition are not particularly limited and can be properly selected depending on a desired object. For example, the cosmetic composition can be prepared in one or more formulations selected from the group consisting of skin toner (skin lotion and milk lotion), nourishing skin toner, essence, nourishing cream, massage cream, makeup base, foundation, pack, essence, eye cream, eye essence, cleansing cream, cleansing foam, cleansing water, cleanser, body lotion, body cream, body oil and body essence, but they are not limited thereto.

EMBODIMENTS

Hereinafter, the constitution and effect of the present invention will be explained in more detail with reference to the examples and drawings. However, these examples and drawings are provided only for the purpose of the examples in order to help the understanding of the present invention, and the scope and range of the present invention are not limited thereto.

Test Example 1

As one example of the present invention, the cosmetic composition of the multiple emulsion formulation comprising the composition of Table 1 was prepared according to the following method.

First, the polymer emulsification, which is the first emulsification, was performed by introducing a moisturizing agent, ethanol and a thickener into purified water, which are aqueous ingredients in the following Table 1, and dispersing them, and then introducing oil (emollient) into the outer phase, and thereafter, stirring them at a room temperature at 3600 rpm for 3 minutes with a homomixer. Thereafter, the neutralizer was introduced to prepare particles of the inner and outer phases having an average particle size of about 5 μm or less. After then, the HIPE (high internal phase emulsion) emulsification, which is the second emulsification, was performed by slowly introducing the prepared particles of the inner and outer phases into the silicon-based surfactant and silicon oil, which are the outermost phase, and paddle-mixing them, and then stirring with the homomixer to prepare a composition of an O/W/S emulsion formulation.

In the following table, the amounts of the respective ingredients refer to wt. % with respect to the total weight of the composition.

TABLE 1

|  |  | Example 1 |
|---|---|---|
| Solvent | Purified water (D.I. WATER) | TO 100 |
| Moisturizing agent | Glycerin | 13 |
| Moisturizing agent | Butylene glycol | 7 |
| Solvent | Ethanol | 7 |
| Thickener | Acrylates/C10-30 alkyl acrylate crosspolymer | 0.09 |
| Thickener | Carbomer | 0.09 |
| Emollient | Squalane | 7 |
| Neutralizer | Tromethamine | 0.09 |
| Silicon Surfactant | Cyclopentasiloxane/dimethicone/ dimethicone/PEG-10/15 crosspolymer | 3 |
| Silicon Surfactant | Cetyl PEG/PPG-10/1 dimethicone/ pentaerythrityl tetra-di-t-butyl hydroxyhydrocinnamate | 0.3 |
| Silicon oil | Dimethicone | 10 |

The average particle size of the droplets comprised in the prepared Example 1 was about 20 μm. FIG. 4 is imaging of Example 1 using microscope (Nikon, Model name: Eclipse 80i Microscope). As illustrated in FIG. 4, it can be verified that the cosmetic composition according to one embodiment of the present invention has the multiple emulsion formulation comprising the inner phase—the outer phase—the outermost phase, and has a structure where a distance between the droplets comprising the inner phase and the outer phase is 5 μm or less, which is very adjacent to each other.

Test Example 2

As one example, in order to verify a difference of formulation stability according to the composition of the droplets comprising the inner phase and the outer phase comprised in the composition of the present invention, the following test was conducted.

First, other compositions were prepared by separating only the aqueous part which can be frozen when freezing from Table 1 of the [Test Example 1] and adjusting the composition of the ethanol and the moisturizing agent as shown in Table 2. Thereafter, the respective prepared compositions were stored in a refrigerator at −15° C. for 4 weeks. The respective amounts in the following table refer to wt. % with respect to 100 wt. % of the total weight of the separated aqueous part.

TABLE 2

|  | Example 2 | Example 3 | Example 4 | Example 5 | Example 6 | Example 7 | Example 8 |
|---|---|---|---|---|---|---|---|
| Purified water (D.I. WATER) | 89 | 87 | 85 | 80 | 77 | 75 | 73 |
| GLYCERIN | 1 | 3 | 5 | 10 | 13 | 13 | 13 |
| BUTYLENE GLYCOL | 7 | 7 | 7 | 7 | 7 | 7 | 7 |
| ETHANOL | 3 | 3 | 3 | 3 | 3 | 5 | 7 |

Figure 5:
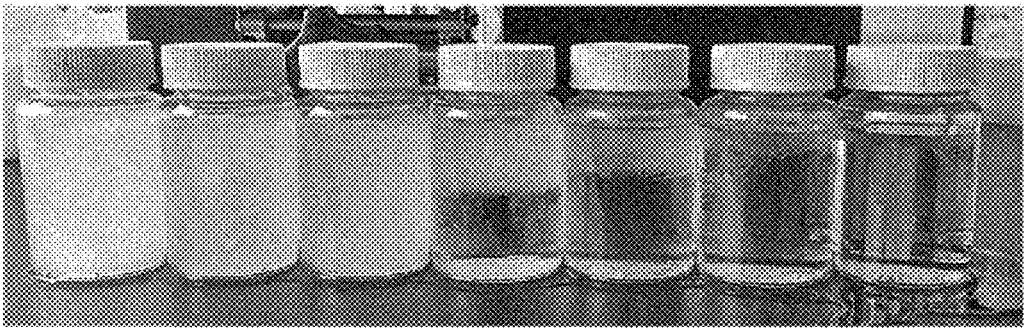
FIG. 5 is a photograph showing the result of the comparison test of the freezing point and the formulation stability according to the amounts of polyol and ethanol comprised in the composition as one embodiment of the present invention (from the left, Example 1, Example 2, Example 3, Example 4, Example 5, Example 6, Example 7, and Example 8).

The result shows that, as shown in FIG. 5, as the amounts of polyol and ethanol become higher, the melting point becomes low, so the formulation of the composition was maintained stably and was transparent. This means that when preparing the cosmetic composition of the multiple emulsion formulation according to the present invention, as the amounts of polyol and ethanol become higher within the predetermined range, no expansion of the inner phase and the outer phase occurs, and thereby the droplets are not broken, and the formulation can be maintained stably.

Test Example 3

As one example, in order to verify a difference of formulation stability according to the average distance between the adjacent droplets comprised in the composition of the present invention, the following test was conducted.

The cosmetic compositions of the multiple emulsion formulation were prepared by preparing droplet particles comprising the inner phase and the outer phase with the composition as shown in Example 1 of Table 1, and then introducing them into a silicon-based surfactant and silicon oil, which are the outermost phase part, such that the amounts of the particles are 30 wt. %, 50 wt. %, 70 wt. %, 80 wt. %, 85 wt. % and 90 wt. %, respectively, with respect to the total weight of the composition (Table 3).

The respective prepared cosmetic compositions were photographed with a microscope (Nikon®, Model: Eclipse 80i Microscope), and the distance between the two adjacent droplets observed in the microscopy image was analyzed, and herein, the distance between the droplets was calculated by Equation 1.

$$\text{Distance between the droplets} = (A) - (r+R) \quad \text{[Equation 1]}$$

where in Equation 1, A represents a distance between the centers of the two adjacent droplets measured 24 hours after the preparation of the composition, and r and R represent the respective radius of the two adjacent droplets measured on the same line as A.

In the following table, the amounts of the respective ingredients refer to wt. % with respect to the total weight of the composition.

TABLE 3

| | Comparative example 1 | Comparative example 2 | Comparative example 3 | Comparative example 4 | Example 9 | Example 10 |
|---|---|---|---|---|---|---|
| Amounts of inner phase and outer phase (wt. %) | 30 | 50 | 70 | 80 | 85 | 90 |
| Cyclopentasiloxane/ dimethicone/ dimethicone/PEG-10/15 crosspolymer | 3 | 3 | 3 | 3 | 3 | 3 |
| Cetyl PEG/PPG-10/1 dimethicone/ pentaerythrityl tetra-di-t-butyl hydroxyhydrocinnamate | 0.3 | 0.3 | 0.3 | 0.3 | 0.3 | 0.3 |
| Dimethicone | 66.7 | 46.7 | 26.7 | 16.7 | 11.7 | 6.7 |
| Stability | Separated immediately after the preparation | Separated immediately after the preparation | Separated immediately after the preparation | Separated | Stable | Stable |
| Average value (μm) of the distance between two adjacent droplets | More than 5 μm | More than 5 μm | More than 5 μm | More than 5 μm | 5 μm or less | 5 μm or less |
| Total sum of the area of the droplets with respect to the entire area of microscopy image | Less than 80% | Less than 80% | Less than 80% | Less than 80% | 80% or more | 80% or more |

Figure 6:
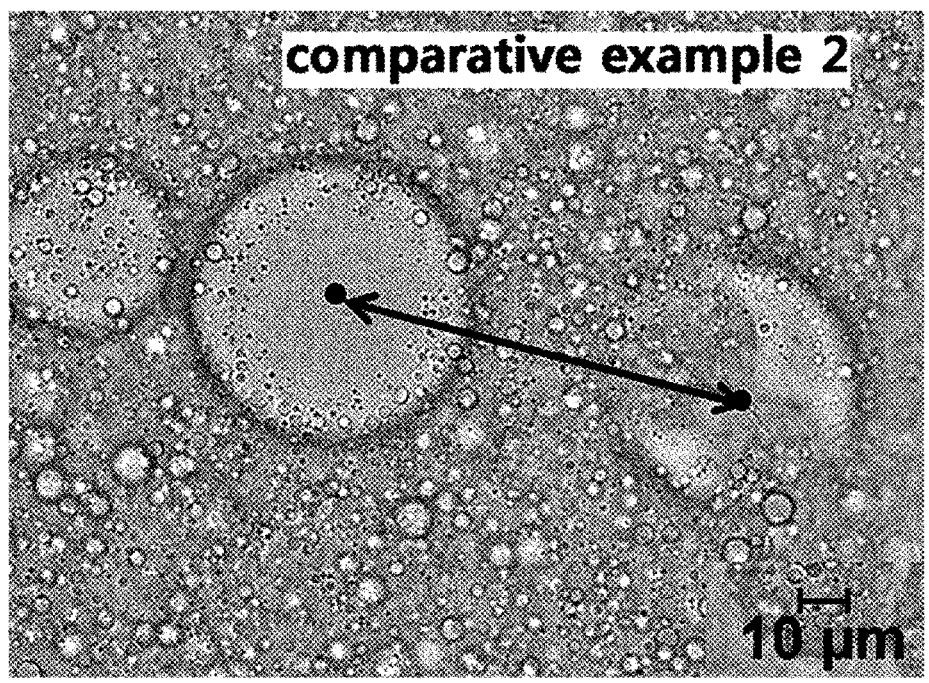
FIG. 6 is a microscopy image of Comparative Example 2 of the present invention. The arrow line is an example of the reference line for measuring a distance between the adjacent particles in the formulation.
Figure 7:
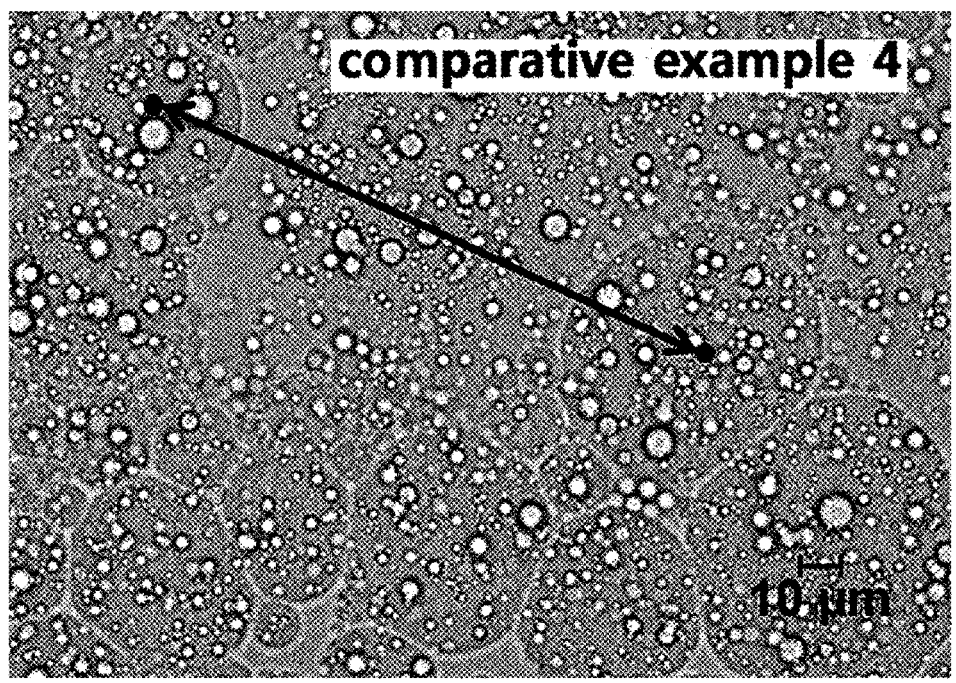
FIG. 7 is a microscopy image of Comparative Example 4 of the present invention. The arrow line is an example of the reference line for measuring a distance between the adjacent particles in the formulation.
Figure 8:
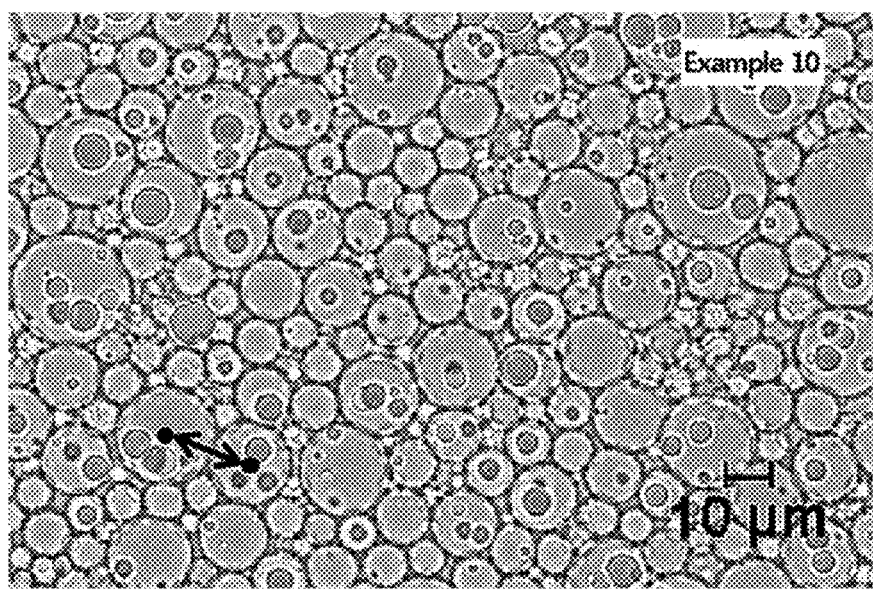
FIG. 8 is a microscopy image of Example 10 which is an embodiment of the present invention. The arrow line is an example of the reference line for measuring a distance between the adjacent particles in the formulation.
Figure 9:
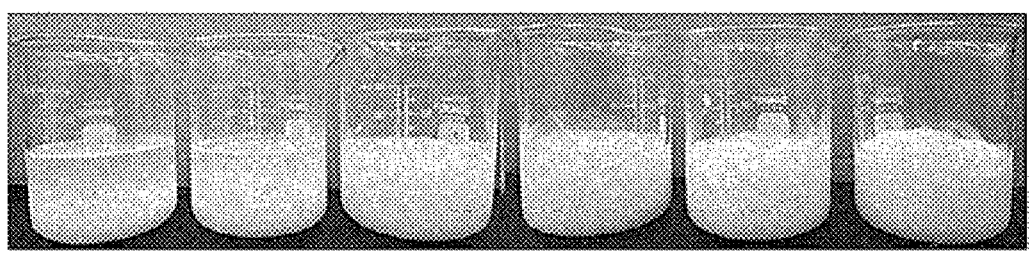
FIG. 9 is a photograph showing the test result of the comparison of the formulation stability of the composition according to the embodiments of the present invention (from the left, Comparative Example 1, Comparative Example 2, Comparative Example 3, Comparative Example 4, Example 9, and Example 10).
Figure 10:
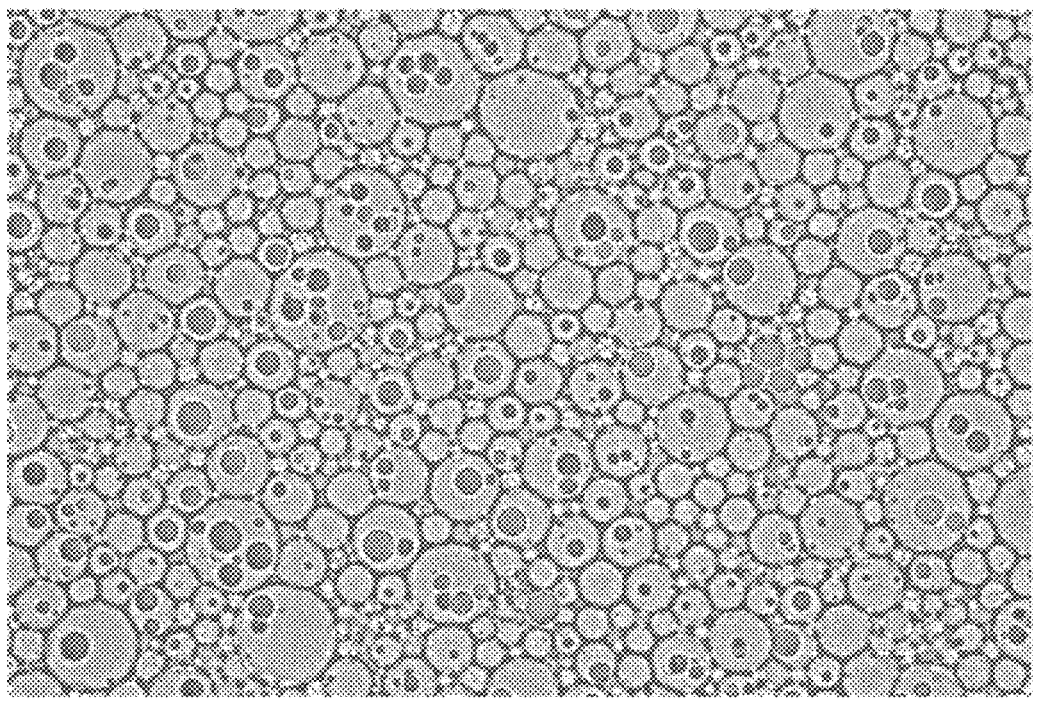
FIG. 10 shows the portions other than the droplets in blue, in the microscopy image of FIG. 8.

FIG. 6 is a microscopy image taken by stirring and sampling the separated contents for microscopic photographing after the preparation of Comparative Example 2, FIG. 7 is a microscopy image taken by stirring and sampling the separated contents for microscopic photographing after the preparation of Comparative Example 4, and FIG. 8 is a microscopy image taken by stirring and sampling the separated contents for microscopic photographing after the preparation of Example 10, wherein the arrow line is the line drawn to pass through the center of the particles of the adjacent droplets in order to measure the distance between the particles. As the result, as shown in FIG. 9, in the case of the formulations (Comparative Examples 1 to 3) wherein the distance between the adjacent droplets comprised in the composition is more than 5 μm and the total sum of the areas of the droplets is already less than 80% with respect to the entire area, a phase separation phenomenon was observed immediately after the preparation, and in the case of Comparative Example 4, a separation phenomenon was observed after 1 hour at 25° C. However, it can be verified that in the formulation wherein the distance between the adjacent droplets is 5 μm or less (Example 10), which is one embodiment of the present invention, a separation phenomenon was not observed, and thus, the formulation was maintained stably. The total sum of the areas of the droplets was calculated using the Image-Pro® 10 Image Analysis Software (Manufacturer: MEDIA CYBERNETICS) program. In the microscopy image of Example 10, in order to calculate the total sum of the areas of the droplets with respect to the entire area of the image, the image was converted to black and white, then a threshold was applied to extract only a portion above a certain value, i.e., the region other than the droplets, and the percentage of this area was calculated. FIG. 10 shows the portions other than the droplets in blue, in the image. The total pixels of the image file were 640×480 px$^2$=307200 px$^2$, and the measured value in the blue area was 35976 px$^2$ (rounded to the fourth decimal point), which was 11.72% of the total area. From this, it can be seen that the total area of the droplets is 88.28% with respect to the total area of the microscope image of FIG. 10.

Test Example 4

Greasy feeling and thickness feeling, which are feelings in using the composition according to one embodiment of the present invention, were verified by sensory evaluation using the T-CATA (Temporal Check-All-That-Apply) technique.

As the embodiment of the present invention, the Example 1 was used. As the comparative example, a W/S emulsion composition comprising the composition of the following [Table 4] (Comparative Example 5) was prepared according to the preparation method typically used.

In the following table, the amounts of the respective ingredients refer to wt. % with respect to the total weight of the composition.

TABLE 4

| | Comparative Example 5 |
|---|---|
| Purified water (Water) | To 100 |
| Glycerin | 15 |
| Sodium chloride | 1 |
| Ethanol | 7 |
| Cyclopentasiloxane/dimethicone/dimethicone/ PEG-10/15 crosspolymer | 3 |
| Dimethicone | 10 |
| Cetyl PEG/PPG-10/1 dimethicone/pentaerythrityl tetra-di-t-butyl hydroxyhydrocinnamate | 0.3 |
| Ethylhexylglycerin | 0.05 |

Evaluation of Greasy Feeling 6 panels of skin care experts evaluated the greasy feeling of Example 1 and Comparative Example 5 twice. A forearm was indicated with a circle having a diameter of 5 cm, and 50 μl of the respective compositions were dispersed on the certain zone and applied by rolling for 2 minutes using an index finger, and then it was evaluated whether the corresponding property was perceived every 5 seconds for 120 seconds.

Figure 11:
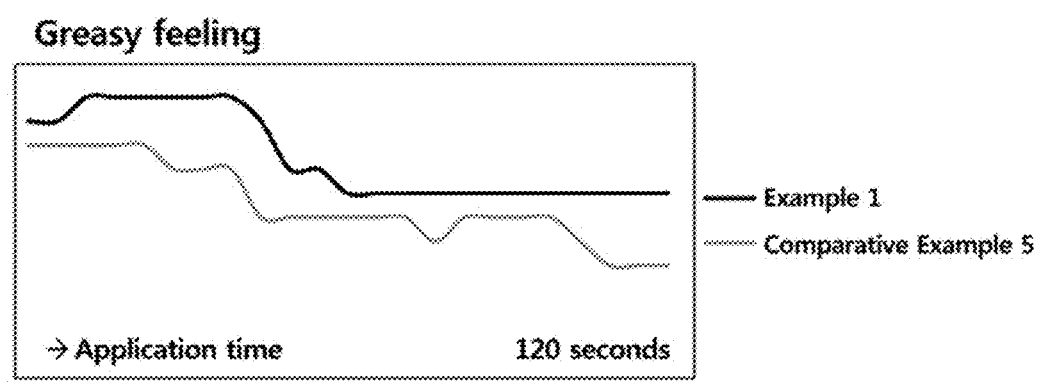
FIG. 11 is a diagram showing the test result of the comparison of greasy feeling between the comparative example and one example of the present invention.

As the result, as shown in FIG. 11, greasy feeling of Comparative Example 5 was continuously decreased for the evaluation time of 120 seconds, whereas greasy feeling of Example 1 was increased as the oil in water particle bursts 10 seconds after the application and oil comprised in the outermost phase is in contact with skin, and due to the oil, greasy feeling was not decreased even 40 seconds after the application. This means that the present invention provides high moisturizing effects.

Evaluation of Thickness Feeling 6 panels of skin care experts evaluated the thickness feeling of Example 1 and Comparative Example 5 twice. A forearm was indicated with a circle having a diameter of 5 cm, and 50 μl of the respective compositions were dispersed on the certain zone and applied by rolling for 2 minutes using an index finger, and then it was evaluated whether the corresponding property was perceived every 5 seconds for 120 seconds.

Figure 12:
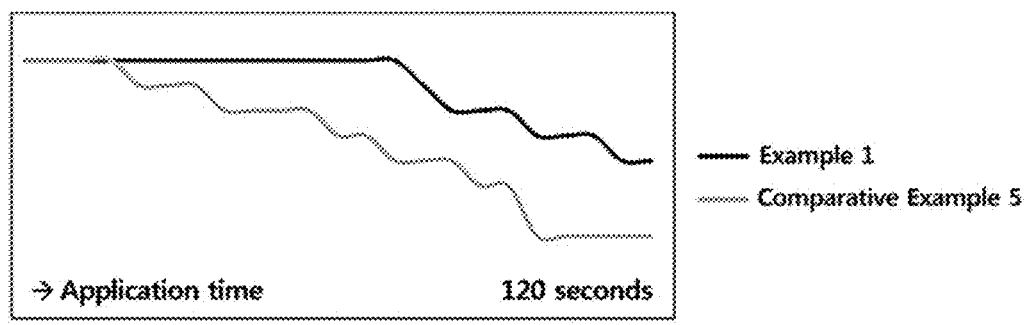
FIG. 12 is a diagram showing the result of the comparison of thickness feeling between the comparative example and one example of the present invention.

As the result, as shown in FIG. 12, thickness feeling of Comparative Example 5 was sharply decreased after applying the composition, whereas the thickness feeling of Example 1 was maintained till 80 seconds after the application, and the thickness feeling was maintained even 120 seconds after the application to be higher than that of Comparative Example 5. This means that oil comprised in the outermost phase of the composition according to one embodiment of the present invention provides high moisturizing effects.

Test Example 5

As one embodiment of the present invention, the cosmetic composition of the multiple emulsion formulation, comprising, as an effective ingredient, thymol trimethoxycinnamate (Melasolv™, AMOREPACIFIC CORPORATION) in the inner phase, was prepared with the composition of Table 5. The preparation method is the same as that for Test Example 1, except that the first emulsification temperature was a high temperature of 70° C.

In the following table, the amounts of the respective ingredients refer to wt. % with respect to the total weight of the composition.

TABLE 5

| | | Example 10 |
|---|---|---|
| Solvent | Purified water (D.I. water) | TO 100 |
| Moisturizing agent | Glycerin | 13 |
| Moisturizing agent | Butylene glycol | 7 |
| Solvent | Ethanol | 7 |
| Thickener | Acrylates/C10-30 alkyl acrylate crosspolymer | 0.09 |
| Thickener | Carbomer | 0.09 |
| Emollient | Caprylic/capric triglyceride | 4 |
| Emollient | Cetyl ethylhexanoate | 3 |
| Whitening main ingredient | Thymol trimethoxycinnamate | 0.1 |
| Neutralizer | Tromethamine | 0.09 |
| Silicon Surfactant | Cyclopentasiloxane/dimethicone/ Dimethicone/PEG-10/15 crosspolymer | 3 |

TABLE 5-continued

| | | Example 10 |
|---|---|---|
| Silicon Surfactant | Cetyl PEG/PPG-10/1 dimethicone/ pentaerythrityl tetra-di-t-butyl hydroxyhydrocinnamate | 0.3 |
| Silicon oil | Dimethicone | 10 |

As the comparative example for verifying the improved formulation stability of the prepared Example 10, a typical O/W emulsion composition (Comparative Example 6) was prepared. While storing the compositions of the multiple emulsion (O/W/S) formulation of Example 10 and the typical emulsion (W/S) formulation of Comparative Example 6 for 12 weeks under the harsh condition at 40° C., the precipitation titers of Melasolv™, which is the effective ingredient comprised in the inner phase of the respective formulations, were observed. The following Table 6 shows wt. % of Melasolv™ with respect to the initial weight of Melasolv™ 4 weeks, 8 weeks, 12 weeks, 16 weeks and 24 weeks after the storage as an average value obtained by experiments repeated three times. From the fact that in the multi-emulsification (O/W/S) formulation of Example 10, wt. % of Melasolve™ with respect to the initial weight of Melasolve™ was maintained close to 100 wt. %, it can be seen that Melasolve™ was not precipitated and was stably comprised in the formulation. The change in wt. % of Melasolve™ over time was caused by sample extraction and experimental deviation, and the actual content did not change.

TABLE 6

| | 4 weeks | 8 weeks | 12 weeks | 16 weeks | 24 weeks |
|---|---|---|---|---|---|
| Example 10 (O/W/S) | 95.80 wt. % | 98.60 wt. % | 99.20 wt. % | 98.90 wt. % | 99.10 wt. % |

Figure 13:
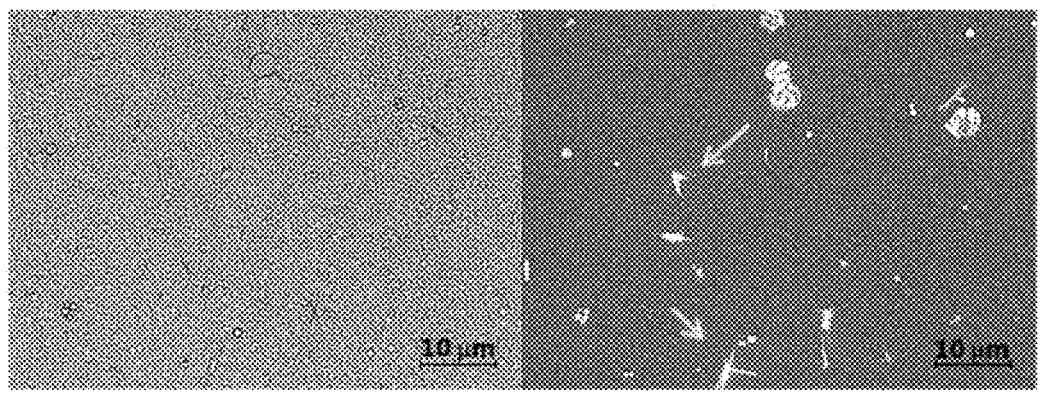
FIG. 13 is a microscopy image showing the result of the precipitation titers of the effective ingredients in the formulation of the comparative example of the present invention (scale bar 10 μm).
Figure 14:
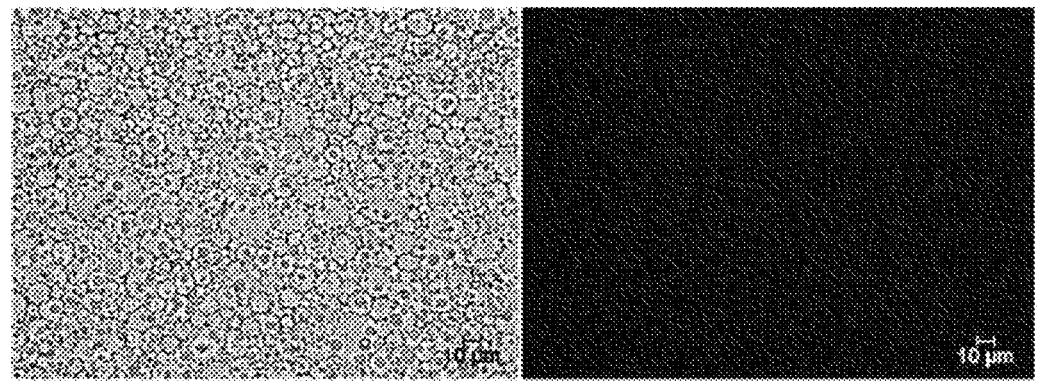
FIG. 14 is a microscopy image showing the result of the precipitation titers of the effective ingredients in the formulation of the example of the present invention (scale bar 10 μm).

Next, while storing the compositions of the multiple emulsion (O/W/S) formulation of Example 10 and the typical emulsion (W/S) formulation of Comparative Example 6 at a low temperature of −20° C., the precipitation titers of Melasolv™, which is the effective ingredient comprised in the inner phase of the respective formulations, were observed using a microscope (Nikon®, Model: Eclipse 80i Microscope). The right image is a polarization image of the left image. As the result, in the typical emulsion (W/S) formulation of Comparative Example 6, precipitation (arrow) of Melasolv™ was observed 2 weeks after the storage at a low temperature (FIG. 13), whereas in the multiple emulsion (O/W/S) formulation of Example 10, Melasolv™ was not precipitated even 4 weeks after the storage at a low temperature (FIG. 14). This means that the multiple emulsion formulation of the present invention can stably comprise the effective ingredient such as Melasolv™, which has a low solubility and precipitation occurs well due to that, without precipitation. The present invention can provide the following embodiments as one example.

The first embodiment may provide a cosmetic composition of a multiple emulsion formulation, comprising: droplets comprising an inner phase and an outer phase; and an outermost phase, wherein said cosmetic composition satisfies one or more of following (i) to (iii):

(i) a distance between two adjacent droplets distributed in the formulation is 5 μm or less, and the distance is calculated for droplets with an average particle size of 2 μm to 50 μm, the distance between the droplets being calculated by the following Equation 1:

$$\text{Distance between the droplets} = (A) - (r+R) \qquad \text{[Equation 1]}$$

where in Equation 1, A represents a distance between the centers of the two adjacent droplets of the composition, and r and R represent the respective radius of the two adjacent droplets measured on the same line as A;

(ii) in a microscopy image obtained by taking a photography of the composition, the sum of the areas of the droplets distributed in the formulation with respect to 100% of the total area of the image is 80% or more and less than 100%, the microscopy image being taken at a magnification of 1000; and (iii) the amount of the droplets comprising the inner phase and the outer phase is greater than 80 wt. % to less than 100 wt. % with respect to the total weight of the composition.

The second embodiment may provide the cosmetic composition according to the first embodiment, wherein the multiple emulsion formulation comprises the inner phase which is an oil phase; the outer phase which is an aqueous phase; and the outermost phase comprising silicon-based oil.

The third embodiment may provide the cosmetic composition according to the first embodiment or the second embodiment, wherein the inner phase comprises one or more oils of ester-based oils, hydrocarbon-based oils, oils of natural origin, and silicon-based oils.

The fourth embodiment may provide the cosmetic composition according to any one of the first embodiment to the third embodiment, wherein the inner phase comprises one or more oils selected from the group consisting of squalane, caprylic/capric triglyceride, cetyl ethylhexanoate, 2-octyldodecanol, and pentaerythritol tetra-2-ethylhexanoate.

The fifth embodiment may provide the cosmetic composition according to any one of the first embodiment to the fourth embodiment, wherein the inner phase comprises one or more selected from the group consisting of thymol trimethoxycinnamate, oil-soluble vitamin, fat-soluble bioactive ingredient, oil-soluble licorice and polyphenol.

The sixth embodiment may provide the cosmetic composition according to any one of the first embodiment to the fifth embodiment, wherein the oil-soluble vitamin comprises one or more of retinol and tocopherol.

The seventh embodiment may provide the cosmetic composition according to any one of the first embodiment to the sixth embodiment, wherein the fat-soluble bioactive ingredient comprises one or more of linolenic acid and glycolipid.

The eighth embodiment may provide the cosmetic composition according to any one of the first embodiment to the seventh embodiment, wherein the outer phase comprises polyol; or polyol, and one or more of a thickener and a solvent.

The ninth embodiment may provide the cosmetic composition according to any one of the first embodiment to the eighth embodiment, wherein the polyol comprises one or more selected from the group consisting of polyethylene glycol, polypropylene glycol, dipropylene glycol, propylene glycol, butylene glycol, glycerin, polyglycerin-3, propanediol, sorbitol, erythritol, xylitol, maltitol, ethylhexanediol, 1,2-hexanediol, PEG/PPG/polybuthylene glycol-8/5/3 glycerin and pentylene glycol.

The tenth embodiment may provide the cosmetic composition according to any one of the first embodiment to the ninth embodiment, wherein the amount of the polyol satisfies one or more of 1 wt. % to 30 wt. % with respect to the total weight of the composition; and 5 wt. % to 35 wt. % with respect to the total weight of the outer phase.

The eleventh embodiment may provide the cosmetic composition according to any one of the first embodiment to the tenth embodiment, wherein the solvent comprises one or more of water and ethanol.

The twelfth embodiment may provide the cosmetic composition according to any one of the first embodiment to the eleventh embodiment, wherein the amount of ethanol satisfies one or more of 3 wt. % to 10 wt. % with respect to the total weight of the composition; and 5 wt. % to 12 wt. % with respect to the total weight of the outer phase.

The thirteenth embodiment may provide the cosmetic composition according to any one of the first embodiment to the twelfth embodiment, wherein the thickener comprises one or more of polyacrylate-based polymer and natural thickeners.

The fourteenth embodiment may provide the cosmetic composition according to any one of the first embodiment to the thirteenth embodiment, wherein the polyacrylate-based polymer comprises one or more selected from the group consisting of carbomer, acrylate/C10-30 alkyl acrylate crosspolymer, ammonium acryloyl dimethyltaurate/VP copolymer, hydroxylethylacrylate/sodium acryloyl dimethyltaurate copolymer, sodium polyacrylate and polyacrylate-13.

The fifteenth embodiment may provide the cosmetic composition according to any one of the first embodiment to the fourteenth embodiment, wherein the thickener comprises carbomer and polyacrylate-based polymer having a hydrophobic chain.

The sixteenth embodiment may provide the cosmetic composition according to any one of the first embodiment to the fifteenth embodiment, wherein the weight ratio of carbomer and polyacrylate-based polymer having a hydrophobic chain is 1:0.5 to 1.5.

The seventeenth embodiment may provide the cosmetic composition according to any one of the first embodiment to the sixteenth embodiment, wherein the amount of the thickener satisfies one or more of 0.01 to 1.0 wt. % with respect to the total weight of the composition; and 0.02 to 1.3 wt. % with respect to the total weight of the outer phase.

The eighteenth embodiment may provide the cosmetic composition according to any one of the first embodiment to the seventeenth embodiment, wherein the silicon-based oil comprises one or more selected from the group consisting of dimethicone, trimethicone, methyltrimethicone, phenyltrimethicone, amodimethicone, cyclomethicone, dimethiconol, vinyldimethicone, propoxytetramethylpiperidinyl dimethicone, cyclotetrasiloxane, cyclopentasiloxane, cyclohexasiloxane, methyletherdimethylsilane and a copolymer thereof.

The nineteenth embodiment may provide the cosmetic composition according to any one of the first embodiment to the eighteenth embodiment, wherein an interface of the outermost phase and the outer phase further comprises a silicon-based surfactant.

The twentieth embodiment may provide the cosmetic composition according to any one of the first embodiment to the nineteenth embodiment, wherein the silicon-based surfactant has an HLB (hydrophile-lipophile balance) of 7 or less.

The twenty-first embodiment may provide the cosmetic composition according to any one of the first embodiment to the twentieth embodiment, wherein the silicon-based surfactant comprises one or more selected from the group consisting of cyclopentasiloxane/dimethicone/dimethicone/

PEG-10/15 crosspolymer, cetyl PEG/PPG-10/1 dimethicone/pentaerythrityl tetra-di-t-butyl hydroxyhydrocinnamate, lauryl dimethicone/polyglycerin-3 crosspolymer, lauryl polyglyceryl-3 polydimethylsiloxyethyl dimethicone, polyglyceryl-3 polydimethylsiloxyethyl dimethicone, polyglyceryl-3 disiloxane dimethicone and dimethicone/polyglycerin-3 crosspolymer.

The twenty-second embodiment may provide the cosmetic composition according to any one of the first embodiment to the twenty-first embodiment, wherein the outermost phase does not comprise a thickener.

The twenty-third embodiment may provide the cosmetic composition according to any one of the first embodiment to the twenty-second embodiment, wherein the total amount of the inner phase and the outer phase is 85 wt. % to 95 wt. % with respect to the total weight of the composition.

The twenty-fourth embodiment may provide the cosmetic composition according to any one of the first embodiment to the twenty-third embodiment, wherein the cosmetic composition is for skin moisturizing.

The twenty-fifth embodiment may provide the use of the cosmetic composition according to any one of the first embodiment to the twenty-fourth embodiment, as a cosmetic.

The twenty-sixth embodiment may provide the use of the cosmetic composition according to the twenty-fifth embodiment, wherein the cosmetic is for skin moisturizing.

The twenty-seventh embodiment may provide a method for preparing the cosmetic composition according to any one of the first embodiment to the twenty-fourth embodiment, comprising a step of preparing droplets by introducing an inner phase into an outer phase; and a step of stabilizing by introducing the droplets into the outermost phase.

The twenty-eighth embodiment may provide the preparation method according to the twenty-seventh embodiment, wherein the step of preparing droplets comprises a first emulsifying step of preparing oil-in-water droplets by introducing an outer phase ingredient comprising polyol and a thickener into a solvent as the outer phase and dispersing it, and then introducing an oil ingredient comprising oil, etc. into the outer phase.

The twenty-ninth embodiment may provide the preparation method according to one or more of the twenty-seventh embodiment and the twenty-eighth embodiment, wherein the first emulsifying step comprises, for example, introducing the oil into the outer phase and stirring it at 2,000 to 5,000 rpm for 1 to 5 minutes.

The thirtieth embodiment may provide the preparation method according to one or more of the twenty-seventh embodiment to the twenty-ninth embodiment, wherein the step of stabilizing comprises a second emulsifying step of stabilizing by introducing the droplets into the outermost phase comprising silicon-based oil and a silicon-based surfactant.

The thirty-first embodiment may provide the preparation method according to any one of the twenty-seventh embodiment to the thirtieth embodiment, wherein the second emulsifying step is carried out by the HIPE (high internal phase emulsion) emulsification method.

The invention claimed is:

1. A cosmetic composition of a multiple emulsion formulation, comprising:
droplets comprising an oil phase as an inner phase and an aqueous phase as an outer phase; and
an outermost phase comprising a silicon-based oil,
wherein said cosmetic composition satisfies following (iii), (i) and (iii), (ii) and (iii), or (i) to (iii):
(i) a distance between two adjacent droplets distributed in the formulation is 5 μm or less, and the distance is calculated for droplets with an average particle size of 2 μm to 50 μm, the distance between the droplets being calculated by the following Equation 1:

$$\text{Distance between the droplets} = (A) - (r+R) \quad \text{Equation 1}$$

where in Equation 1, A represents a distance between centers of the two adjacent droplets of the cosmetic composition, and r and R represent respective radius of the two adjacent droplets measured on the same line as A;
(ii) in a microscopy image obtaining by taking a photograph of the cosmetic composition, a sum of areas of the droplets distributed in the formulation with respect to a total area of the microscopy image is 80% or more and less than 100%, the microscopy image being taken at a magnification of 1000; and
(iii) a total amount of the droplets comprising the inner phase and the outer phase is greater than 80 wt. % to less than 100 wt. % with respect to a total weight of the cosmetic composition,
wherein the outer phase comprises a polyol, and one or more of a thickener and a solvent,
wherein an amount of the polyol satisfies one or more of 1 wt. % to 30 wt. % with respect to the total weight of the cosmetic composition; and 5 wt. % to 35 wt. % with respect to a total weight of the outer phase, and
wherein an amount of the solvent satisfies one or more of 3 wt. % to 10 wt. % with respect to the total weight of the cosmetic composition; and 5 wt. % to 12 wt. % with respect to a total weight of the outer phase.

2. The cosmetic composition according to claim 1, wherein the inner phase comprises one or more oils of an ester-based oil, a hydrocarbon-based oil, an oil of natural origin, and a silicon-based oil.

3. The cosmetic composition according to claim 2, wherein the inner phase comprises the one or more oils selected from the group consisting of squalane, caprylic/capric triglyceride, cetyl ethylhexanoate, 2-octyldodecanol, and pentaerythritol tetra-2-ethylhexanoate.

4. The cosmetic composition according to claim 1, wherein the inner phase comprises one or more selected from the group consisting of thymol trimethoxycinnamate, an oil-soluble vitamin, a fat-soluble bioactive ingredient, an oil-soluble licorice, and a polyphenol.

5. The cosmetic composition according to claim 4, wherein the oil-soluble vitamin comprises one or more of retinol and tocopherol.

6. The cosmetic composition according to claim 4, wherein the fat-soluble bioactive ingredient comprises one or more of linolenic acid and glycolipid.

7. The cosmetic composition according to claim 1, wherein the polyol comprises one or more selected from the group consisting of polyethylene glycol, polypropylene glycol, dipropylene glycol, propylene glycol, butylene glycol, glycerin, polyglycerin-3, propanediol, sorbitol, erythritol, xylitol, maltitol, ethylhexanediol, 1,2-hexanediol, PEG/PPG/polybuthylene glycol-8/5/3 glycerin, and pentylene glycol.

8. The cosmetic composition according to claim 1, wherein the solvent comprises one or more of water and ethanol.

9. The cosmetic composition according to claim 1, wherein the thickener comprises one or more of a polyacrylate-based polymer and a natural thickener.

10. The cosmetic composition according to claim 9, wherein the polyacrylate-based polymer comprises one or more selected from the group consisting of a carbomer, an acrylate/C10-30 alkyl acrylate crosspolymer, an ammonium acryloyl dimethyltaurate/vinylpyrrolidone(VP) copolymer, a hydroxylethylacrylate/sodium acryloyl dimethyltaurate copolymer, a sodium polyacrylate, and polyacrylate-13.

11. The cosmetic composition according to claim 1, wherein the thickener comprises a carbomer and a polyacrylate-based polymer having a hydrophobic chain.

12. The cosmetic composition according to claim 11, wherein a weight ratio of the carbomer and the polyacrylate-based polymer having a hydrophobic chain is 1:0.5 to 1.5.

13. The cosmetic composition according to claim 1, wherein an amount of the thickener satisfies one or more of 0.01 to 1.0 wt. % with respect to the total weight of the cosmetic composition; and 0.02 to 1.3 wt. % with respect to a total weight of the outer phase.

14. The cosmetic composition according to claim 1, wherein the silicon-based oil comprises one or more selected from the group consisting of dimethicone, trimethicone, methyltrimethicone, phenyltrimethicone, amodimethicone, cyclomethicone, dimethiconol, vinyldimethicone, propoxytetramethylpiperidinyl dimethicone, cyclotetrasiloxane, cyclopentasiloxane, cyclohexasiloxane, methyletherdimethylsilane and a copolymer thereof.

15. The cosmetic composition according to claim 1, wherein an interface of the outermost phase and the outer phase further comprises a silicon-based surfactant.

16. The cosmetic composition according to claim 15, wherein the silicon-based surfactant has an HLB (hydrophile-lipophile balance) of 7 or less.

17. The cosmetic composition according to claim 15, wherein the silicon-based surfactant comprises one or more selected from the group consisting of cyclopentasiloxane/dimethicone/dimethicone/PEG-10/15 crosspolymer, cetyl PEG/PPG-10/1 dimethicone/pentaerythrityl tetra-di-t-butyl hydroxyhydrocinnamate, lauryl dimethicone/polyglycerin-3 crosspolymer, lauryl polyglyceryl-3 polydimethylsiloxyethyl dimethicone, polyglyceryl-3 polydimethylsiloxyethyl dimethicone, polyglyceryl-3 disiloxane dimethicone and dimethicone/polyglycerin-3 crosspolymer.

18. The cosmetic composition according to claim 1, wherein the outermost phase does not comprise a thickener.

19. The cosmetic composition according to claim 1, wherein a total amount of the inner phase and the outer phase is 85 wt. % to 95 wt. % with respect to the total weight of the composition.

20. A method for skin moisturizing, comprising applying an effective amount of the cosmetic composition according to claim 1 to a subject in need thereof.

21. A method for preparing the cosmetic composition according to claim 1, comprising:
a step of preparing droplets by introducing an inner phase into an outer phase; and
a step of stabilizing the droplets by introducing the droplets into the outermost phase.

22. The method according to claim 21, wherein the step of preparing droplets comprises a first emulsifying step of preparing oil-in-water droplets by introducing an outer phase ingredient comprising polyol and a thickener into a solvent as the outer phase and dispersing it, and then introducing an oil ingredient comprising oil into the outer phase.

23. The preparation method according to claim 22, wherein the first emulsifying step comprises, introducing the oil into the outer phase and stirring it at 2,000 to 5,000 rpm for 1 to 5 min.

24. The method according to claim 21, wherein the step of stabilizing comprises a second emulsifying step of stabilizing by introducing the droplets into the outermost phase comprising a silicon-based oil and a silicon-based surfactant.

25. The method according to claim 24, wherein the second emulsifying step is carried out by HIPE (high internal phase emulsion) emulsification method.

* * * * *